United States Patent
Takagi et al.

(10) Patent No.: US 9,192,354 B2
(45) Date of Patent: Nov. 24, 2015

(54) ULTRASOUND DIAGNOSTIC APPARATUS AND ULTRASOUND DIAGNOSTIC METHOD

(75) Inventors: Kazuya Takagi, Osaka (JP); Satoshi Kondo, Kyoto (JP)

(73) Assignee: KONICA MINOLTA, INC., Tokyo (JP)

( * ) Notice: Subject to any disclaimer, the term of this patent is extended or adjusted under 35 U.S.C. 154(b) by 155 days.

(21) Appl. No.: 13/813,815

(22) PCT Filed: Jun. 5, 2012

(86) PCT No.: PCT/JP2012/003685
§ 371 (c)(1),
(2), (4) Date: Feb. 1, 2013

(87) PCT Pub. No.: WO2012/169177
PCT Pub. Date: Dec. 13, 2012

(65) Prior Publication Data
US 2013/0137984 A1    May 30, 2013

(30) Foreign Application Priority Data
Jun. 7, 2011    (JP) .................. 2011-127505

(51) Int. Cl.
*A61B 8/14* (2006.01)
*A61B 8/00* (2006.01)
*A61B 8/08* (2006.01)

(52) U.S. Cl.
CPC . *A61B 8/14* (2013.01); *A61B 8/085* (2013.01); *A61B 8/469* (2013.01); *A61B 8/5207* (2013.01); *A61B 8/5223* (2013.01)

(58) Field of Classification Search
CPC .......... A61B 8/085; A61B 8/14; A61B 8/469; A61B 8/5207; A61B 8/5223
USPC ................. 600/439, 442, 447, 458
See application file for complete search history.

(56) References Cited

U.S. PATENT DOCUMENTS

| | | | |
|---|---|---|---|
| 5,577,505 | A | 11/1996 | Brock-Fisher et al. |
| 5,632,277 | A | 5/1997 | Chapman et al. |

(Continued)

FOREIGN PATENT DOCUMENTS

| | | |
|---|---|---|
| CN | 101779968 A | 7/2010 |
| JP | 2004-321582 | 11/2004 |

(Continued)

OTHER PUBLICATIONS

International Search Report issued Sep. 11, 2012 in corresponding International Application No. PCT/JP2012/003685.

(Continued)

*Primary Examiner* — Baisakhi Roy
(74) *Attorney, Agent, or Firm* — Holtz, Holtz, Goodman & Chick PC

(57) ABSTRACT

An ultrasound diagnostic apparatus comprising: an image forming unit which forms an ultrasound image that corresponds to an echo signal received from a subject to which a contrast medium has been administered; a region of interest setting unit which sets, in a target region corresponding to target tissue on the ultrasound image formed by the image forming unit, a first region of interest and a second region of interest which are two regions different from each other; a feature value extraction unit which extracts, as a feature value, a difference in brightness between the first region of interest and the second region of interest set by the region of interest setting unit; and a type determination unit which determines, based on the feature value extracted by the feature value extraction unit, a type of the target tissue.

23 Claims, 10 Drawing Sheets

(56) References Cited

U.S. PATENT DOCUMENTS

| | | | |
|---|---|---|---|
| 5,706,819 A | | 1/1998 | Hwang et al. |
| 5,984,870 A | | 11/1999 | Giger et al. |
| 6,547,738 B2 | * | 4/2003 | Lysyansky ............... 600/458 |
| 8,520,927 B2 | | 8/2013 | Satoh et al. |
| 2004/0127794 A1 | * | 7/2004 | Murashita ............... 600/442 |
| 2008/0071174 A1 | * | 3/2008 | Waki et al. ............... 600/442 |
| 2008/0177180 A1 | * | 7/2008 | Azhari et al. ............ 600/439 |
| 2009/0270733 A1 | * | 10/2009 | Koide ..................... 600/447 |
| 2010/0256493 A1 | | 10/2010 | Chono |
| 2013/0230230 A1 | * | 9/2013 | Ajemba et al. ........... 382/133 |

FOREIGN PATENT DOCUMENTS

| | | |
|---|---|---|
| JP | 2007-20731 | 2/2007 |
| JP | 2009-95512 | 5/2009 |
| JP | 2010-5263 | 1/2010 |
| JP | 2011-78514 | 4/2011 |
| WO | 2009/060751 | 5/2009 |

OTHER PUBLICATIONS

Masafumi Kitaoka et al., "Kanshuryuu no Tyouonpa Sindan Kijun (An) (Criteria for ultrasound diagnosis of liver growth (draft))", Japanese journal of medical ultrasonics, vol. 37, No. 2, Mar. 15, 2010, pp. 157-166, http://www.jsum.or.jp/committee/diagnostic/pdf/liver_tumor.pdf, (with partial English translation).

Chinese Office Action (and English translation thereof) dated Mar. 10, 2015, issued in counterpart Chinese Application No. 201280002192.9 X.

* cited by examiner

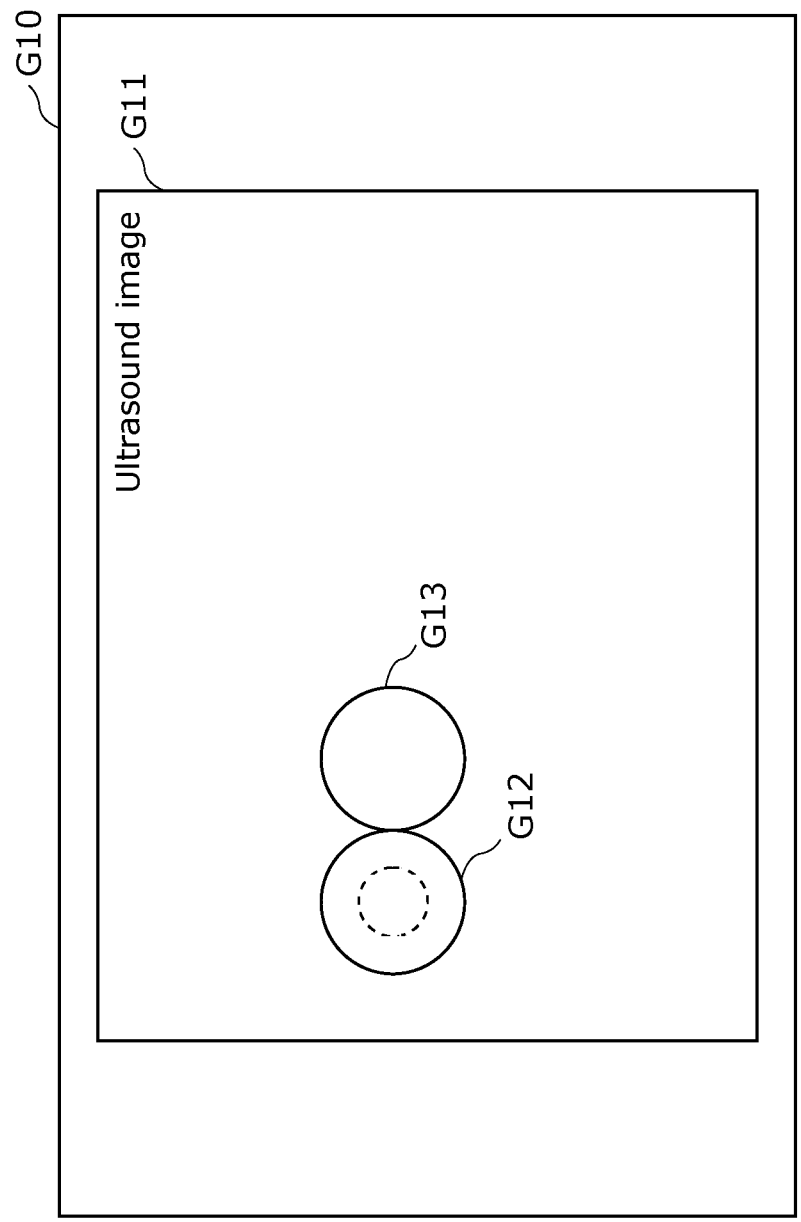

Type determination result

| | | |
|---|---|---|
| Malignant | Hepatoma | 85% |
| | Metastatic hepatic cancer | 15% |
| Benign | Liver hemangioma | 5% |
| | FNH | 5% |

FIG. 4

| | | Vascular phase | | Post vascular phase |
|---|---|---|---|---|
| | | Arterial phase | Portal phase | |
| Malignant | Hepatoma | hyper | iso / hypo | hypo |
| | Metastatic hepatic cancer | ring / hyper | iso / hypo | hypo |
| Benign | Liver hemangioma | ring→ / ring→ | ring→ | hypo |
| | FNH | center→ | iso | iso | hyper  Hyperechoic compared to the surrounding
iso    Isoechoic to the surrounding
hypo   Hypoechoic compared to the surrounding
ring   Ring pattern
center Center pattern

ULTRASOUND DIAGNOSTIC APPARATUS AND ULTRASOUND DIAGNOSTIC METHOD

TECHNICAL FIELD

The present invention relates to ultrasound diagnostic apparatuses and ultrasound diagnostic methods. The present invention particularly relates to an ultrasound diagnostic apparatus and an ultrasound diagnostic method which determine the type of target tissue inside a body of a subject.

BACKGROUND ART

The contrast enhanced ultrasound is one of the image diagnosis methods which can provide high sensitivity image of a blood vessel to which a contrast medium has been administered. At present, in Japan, use of a contrast medium Sonazoid has been approved for liver diagnosis. The contrast medium Sonazoid is used for differentiation of a hepatic tumor.

In the case of a liver diagnosis, existence or absence of a tumor is identified first. In an ultrasound image, the tumor can be identified as a hypoechoic region or a hyperechoic region. Subsequently, the contrast of the tumor is enhanced with administration of the contrast medium.

Currently, the type determination of the tumor is performed based on the subjective judgment of a reader of the ultrasound image, and thus a problem exists that the diagnosis result depends on the reader.

In view of the problem, an objective differentiation method has been disclosed in which the differentiation is performed based on time-sequence variation in two feature values, which are average brightness and the standard deviation, of a tumor region (e.g. Patent Literature (PTL) 1).

According to the technique disclosed in PTL 1, three circles each of which is different in size and includes a tumor are set. The time waveform of the feature value of each of the circle is compared with the typical waveform of each of the types to determine the type based on the typical waveform that best resembles the time waveform. In each of the time phases, the tumor type that is most similar to the feature value of each of the three circles is determined. Then, the tumor type is determined to the type that occurs most.

CITATION LIST

Patent Literature

[PTL 1]
Japanese Unexamined Patent Application Publication No. 2010-005263
[PTL 2]
U.S. Pat. No. 5,632,277
[PTL 3]
U.S. Pat. No. 5,706,819
[PTL 4]
U.S. Pat. No. 5,577,505

Non Patent Literature

[NPL 1]
Kanshuryuu no Tyouonpa Sindan Kijun (An) (Criteria for ultrasound diagnosis of liver growth (draft)), http://www.j-sum.or.jp/committee/diagnostic/pdf/liver_tumor.pdf

SUMMARY OF INVENTION

Technical Problem

The type determination of the tumor is performed based on the subjective judgment of a reader of the ultrasound image, and thus a problem exists that the diagnosis result depends on the reader.

In view of the above, an object of the present invention is to provide an ultrasound diagnostic apparatus or the like which can determine the type of a hepatic tumor with high accuracy without depending on the reader of the ultrasound image.

Solution to Problem

In order to achieve the aforementioned object, an ultrasound diagnostic apparatus according to an aspect of the present invention is an ultrasound diagnostic apparatus which determines a type of target tissue inside a body of a subject, the ultrasound diagnostic apparatus includes: an image forming unit configured to form an ultrasound image which corresponds to an echo signal received from the subject to which a contrast medium has been administered; a region of interest setting unit configured to set, in a target region corresponding to the target tissue on the ultrasound image formed by the image forming unit, a first region of interest and a second region of interest which are two regions different from each other; a feature value extraction unit configured to extract, as a feature value, a difference in brightness between the first region of interest and the second region of interest set by the region of interest setting unit; and a type determination unit configured to determine, based on the feature value extracted by the feature value extraction unit, the type of the target tissue.

These general and specific aspects may be implemented using a system, a method, an integrated circuit, a computer program, or a computer-readable recording medium such as a CD-ROM, or any combination of systems, methods, integrated circuits, computer programs, or computer-readable recording media.

Advantageous Effects of Invention

According to the present invention, it is possible to determine the type of a hepatic tumor with high accuracy without depending on a reader of an ultrasound image.

BRIEF DESCRIPTION OF DRAWINGS

FIG. 3A is an example of a display image according to Embodiment 1.

FIG. 4 is a diagram for describing a contrast enhancement pattern of a hepatic tumor.

DESCRIPTION OF EMBODIMENT

Underlying Knowledge Forming Basis of the Present Invention

In relation to the type determination method disclosed in the Background Art section, the inventors have found the following problem.

FIG. 4 shows typical examples of a contrast enhancement pattern of a hepatic tumor (Non Patent Literature (NPL) 1).

There are generally two time phases in contrast enhancement. One of the time phases of the contrast enhancement is a vascular phase which lasts approximately two minutes after administration of the contrast medium. The other of the time phases is a post vascular phase which is ten minutes after and onward of the administration. The vascular phase is a time phase in which time-series change in contrast enhancement pattern is significant, and the post vascular phase is a time phase in which change is scarce. In more detail, the vascular phase is distinguished into an arterial phase in which inflow from an artery that nourishes the liver is dominant, and a portal phase in which the inflow from a portal vein is dominant. It is said that nourishment of the artery is more dominant and the inflow from the portal vein decreases, when the degree of malignancy of the tumor is higher.

The actual diagnosis is made by observing the time-series change in the contrast enhancement pattern, and determining the tumor type. For example, a hepatoma is suspected when the tumor is hyperechoic compared to parenchyma in the vascular phase and the tumor is hypoechoic compared to parenchyma in the post vascular phase.

At present, the type determination of the tumor is made based on the subjective judgment of the reader of the ultrasound image, and thus a problem exists that the result of the diagnosis depends on the reader.

As shown in FIG. 4, in the actual differentiation of tumor, useful observations includes: difference from the parenchyma; a ring pattern; a center pattern; or a homogeneous pattern.

In view of this, the first method described in PTL 1 determines the contrast enhancement pattern using the standard deviation. However, this can result in incorrect determination because, for example, the center pattern and the ring pattern may have the same standard deviation.

Figure 8:
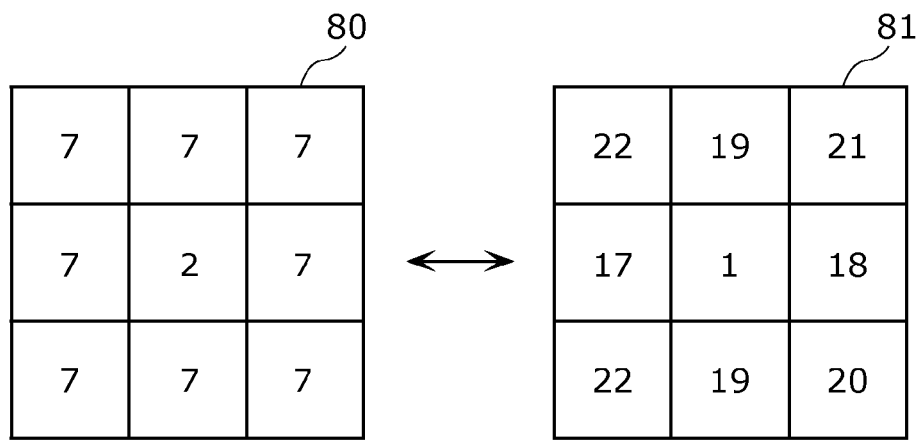
FIG. 8 is a diagram for describing a method for evaluating a pattern of a tumor according to PTL 1.

In contrast, the second method in PTL 1 evaluates a spatial pattern using three circles, and thus can evaluate the pattern of the tumor. FIG. 8 is a diagram for describing the method for evaluating the pattern of the tumor according to PTL 1. The numbers shown in FIG. 8 indicate brightness values of regions within the tumor. The method disclosed in PTL 1 evaluates pattern of the tumor based on difference between an input pattern 81 and a predetermined pattern 80. Here, when the input pattern 81 has a strong ring pattern as shown in FIG. 8, there are cases where the difference between the input pattern 81 and the predetermined pattern 80 is large. Thus, there is a possibility that the strength of the pattern cannot be correctly evaluated.

In view of the above, an object of the present invention is to provide an ultrasound diagnostic apparatus and the like which can perform the type determination of the hepatic tumor with high accuracy.

In order to solve such a problem, an ultrasound diagnostic apparatus according to an aspect of the present invention is an ultrasound diagnostic apparatus which determines a type of target tissue inside a body of a subject, the ultrasound diagnostic apparatus includes: an image forming unit configured to form an ultrasound image which corresponds to an echo signal received from the subject to which a contrast medium has been administered; a region of interest setting unit configured to set, in a target region corresponding to the target tissue on the ultrasound image formed by the image forming unit, a first region of interest and a second region of interest which are two regions different from each other; a feature value extraction unit configured to extract, as a feature value, a difference in brightness between the first region of interest and the second region of interest set by the region of interest setting unit; and a type determination unit configured to determine, based on the feature value extracted by the feature value extraction unit, the type of the target tissue.

With this, it is possible to determine the type of the tumor based on the difference in brightness between the two regions of interest which are set in a target region (tumor region) in the ultrasound image and which show significant feature according to the type of the tumor. At this time, determination is made based on the difference in brightness between the two regions of interest. In this way, the determination result is less likely to be affected by gain or the like of the ultrasound probe, and the strength of the pattern can be accurately evaluated. Thus, it is possible to calculate the difference in brightness between the two regions of interest in the ultrasound image obtained from the subject, and determine the type of the tumor which matches the calculated difference in brightness. Thus, it is possible to determine the type of a hepatic tumor with high accuracy without depending on the reader of an ultrasound image.

Furthermore, for example, the region of interest setting unit is further configured to set a third region of interest outside the target region on the ultrasound image, and the feature value extraction unit is configured to extract, as the feature value, (i) a difference in brightness between the first region of interest and the third region of interest, and (ii) the difference in brightness between the first region of interest and the second region of interest.

With this, it is possible to determine the type of the tumor based on the difference in brightness between the tumor region and the parenchymal region in the ultrasound image. Here, since the tumor region and the parenchymal region are set, the type of the tumor can be determined based on not only the brightness of the tumor region, but also based on the difference in brightness between the tumor region and the parenchymal region. Thus, it is possible to determine the type of the hepatic tumor with high accuracy.

Furthermore, for example, the feature value extraction unit is further configured to extract, as the difference, a brightness gradient having a largest absolute value in a direction (i) toward a surrounding area from a center area in the target region or (ii) toward the center area from the surrounding area in the target region.

With this, it is possible to determine the type of the tumor based on the brightness gradient in a direction toward the surrounding area from the center area of the tumor region (or a direction toward the center area from the surrounding area), without depending on the position or the shape of the center area of the tumor region. Thus, it is possible to determine the type of a hepatic tumor with high accuracy.

Furthermore, for example, the region of interest setting unit is configured to set (i) the second region of interest which is centered on a center area of the target region and is approximately elliptical in shape, and (ii) the first region of interest which is centered on the center area of the target region, is approximately elliptical in shape, includes a region larger than the second region, and excludes the second region of interest.

With this, it is possible to regard the tumor region in the ultrasound image as being approximately elliptical in shape, set the region of interest in each of the center area and the surrounding area of the elliptical shape, calculate the difference in brightness between the regions of interest, and determine the type of the tumor which matches the calculated difference in brightness. Thus, it is possible to determine the type of the hepatic tumor more accurately.

Furthermore, for example, the region of interest setting unit is configured to set (i) the second region of interest which is centered on a center area of the target region and is approximately circular in shape, and (ii) the first region of interest which is centered on the center area of the target region, is approximately circular in shape, includes a region larger than the second region, and excludes the second region of interest.

With this, it is possible to regard the tumor region in the ultrasound image as being approximately circular in shape, set the region of interest in each of the center area and the surrounding area of the circular shape, calculate the difference in brightness between the regions of interest, and determine the type of the tumor which matches the calculated difference in brightness. Thus, it is possible to determine the type of the hepatic tumor more accurately.

Furthermore, for example, the feature value extraction unit is configured to extract, as the feature value, (i) a distance between a center area of the target region and a position at which an absolute value of brightness gradient is largest in a direction toward a surrounding area from the center area in the target region or in a direction toward the center area from the surrounding area in the target region, and (ii) the difference in brightness between the first region of interest and the second region of interest.

With this, it is possible to determine the type of the tumor based on the size of the radius at which the brightness gradient is greatest in a direction toward the surrounding area from the center area in the tumor (or a direction toward the center area from the surrounding area). Thus, it is possible to determine the type of the hepatic tumor with high accuracy.

Furthermore, for example, the region of interest setting unit is configured to (i) set the second region of interest on a side closer to a center area relative to a position at which an absolute value of a brightness gradient is largest in a direction toward a surrounding area from the center area in the target region, and (ii) set the first region of interest on a side further from the center area relative to the position.

With this, it is possible to set, as the regions of interest, two regions having large difference between each other in the average brightness. Use of these two regions of interest makes it possible to increase the accuracy in determining the type of the tumor. Thus, it is possible to determine the type of the hepatic tumor with high accuracy.

Furthermore, for example, the feature value extraction unit is configured to extract, as the feature value, a difference in brightness between the first region of interest and the second region of interest for each of a plurality of time periods, and the type determination unit is configured to determine, based on the feature value of each of the time periods, the type of the target tissue.

With this, the difference in brightness between the regions of interest in a predetermined period (e.g. an arterial phase and the portal phase in the vascular phase; and the post vascular phase) during which the contrast enhancement pattern by the contrast medium is distinctive is used. This increases the accuracy in determining the type of the tumor. Thus, it is possible to determine the type of the hepatic tumor with high accuracy.

Furthermore, for example, the type determination unit is configured to determine, by referring to an association between a plurality of patterns of a feature value and a plurality of types of the target tissue, a type of the target tissue to be a type which corresponds to one of the patterns that matches the feature value extracted by the feature value extraction unit.

With this, it is possible to determine the type of the tumor based on the feature value. A specific example of the association between the predetermined feature value and the type of the target tissue is learning data which is based on the past cases.

Furthermore, for example, the type determination unit is configured to determine, based on the feature value, the type of the target tissue to be one of a hepatoma, a metastatic hepatic cancer, a liver hemangioma, and a focal nodular hyperplasia (FNH).

With this, the feature value appropriate for the type determination of the hepatic tumor is used. Thus, it is possible to determine the representative case of the hepatic tumor, such as the hepatoma, the metastatic hepatic cancer, the liver hemangioma, or the focal nodular hyperplasia (FNH).

These general and specific aspects may be implemented using a system, a method, an integrated circuit, a computer program, or a computer-readable recording medium such as a CD-ROM, or any combination of systems, methods, integrated circuits, computer programs, or computer-readable recording media.

The following describes the ultrasound diagnostic apparatus according to an aspect of the present invention with reference to the drawings.

The exemplary embodiment described below shows a preferable specific example. The numerical values, shapes, materials, structural elements, the arrangement and connection of the structural elements, steps, the processing order of the steps etc. shown in the following exemplary embodiment are mere examples, and therefore do not limit the present invention. Furthermore, among the structural elements in the following exemplary embodiment, structural elements not recited in any one of the independent claims defining the most generic part of the inventive concept of the present invention are described as arbitrary structural elements for configuring a more preferable embodiment.

The following describes a configuration and operations of the system.

Embodiment 1

This embodiment describes an example in which the type of hepatic tumor is determined with high accuracy by introducing a feature value which reflects a feature, such as difference in brightness between the tumor region (target region) and a parenchymal region, a ring pattern, a center pattern, or a homogeneous pattern, in an ultrasound image. It should be noted that a "tumor" indicates tissue which has a different property compared with other tissue, and includes both a benign tumor and a malignant tumor.

Figure 1:
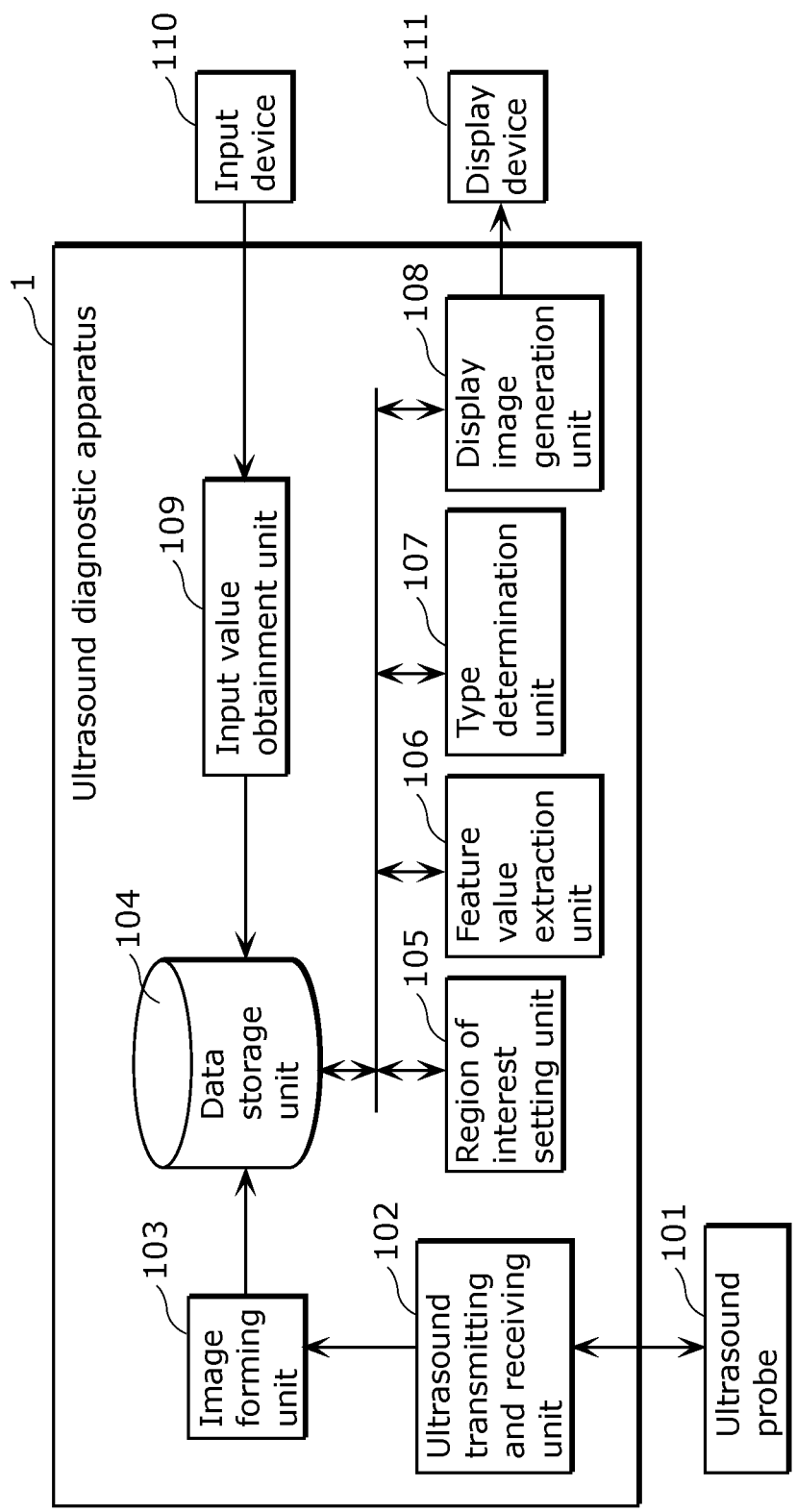
FIG. 1 is a configuration diagram of an ultrasound diagnostic apparatus according to Embodiment 1.

FIG. 1 is a configuration diagram of an ultrasound diagnostic apparatus 1 according to this embodiment.

As shown in FIG. 1, the ultrasound diagnostic apparatus 1 according to this embodiment includes: an ultrasound probe 101, an ultrasound transmitting and receiving unit 102, an image forming unit 103, a data storage unit 104, a region of interest setting unit 105, a feature value extraction unit 106, a type determination unit 107, a display image generation unit 108, an input value obtainment unit 109, an input device 110, and a display device 111.

(Configuration)

The ultrasound probe 101 transforms an electric signal output from the ultrasound transmitting and receiving unit 102 into ultrasound, and transmits the ultrasound to a subject. Then, the ultrasound probe 101 transforms the echo signal, which is a reflection from the subject, into an electric signal, and outputs the electric signal to the ultrasound transmitting and receiving unit 102.

The ultrasound transmitting and receiving unit 102 generates the electric signal which is a source of the ultrasound signal, and outputs the electric signal to the ultrasound probe 101. Furthermore, the ultrasound transmitting and receiving unit 102 transforms the electric signal output from the ultrasound probe 101 into a digital echo signal, and outputs the digital echo signal to the image forming unit 103.

The image forming unit 103 transforms the echo signal output from the ultrasound transmitting and receiving unit 102 into a brightness value, and forms an ultrasound image. Then, the image forming unit 103 stores the formed ultrasound image in the data storage unit 104.

The data storage unit 104 stores an input image, a plane of interest including a tumor, a region of interest used for the type determination, learning data used for the type determination, a feature value of input data used for the type determination, and the like.

The input value obtainment unit 109 obtains information, such as the plane of interest, and the region of interest, designated by an operator via the input device 110, and stores the information in the data storage unit 104.

The region of interest setting unit 105 reads out the plane of interest and the input image from the data storage unit 104, and calculates displacement between the plane of interest and the input image. Subsequently, the region of interest setting unit 105 reads out the region of interest from the data storage unit 104, and corrects the position of the region of interest based on the calculated amount of displacement. Then, the region of interest setting unit 105 stores the corrected region of interest in the data storage unit 104.

The feature value extraction unit 106 reads out the input image and the region of interest from the data storage unit 104, and extracts a predetermined feature value from the region of interest in the input image. Then, the feature value extraction unit 106 arranges the extracted feature values including the feature value in time-series, and stores the arranged feature values in the data storage unit 104.

The type determination unit 107 reads out, from the data storage unit 104, (i) the feature value of a period from the administration of the contrast medium till the post vascular phase, and (ii) learning data for each of the types, and determines the tumor type. After determining the tumor type, the type determination unit 107 stores the result of the type determination in the data storage unit 104.

The display image generation unit 108 reads out, from the data storage unit 104, each of the input image, the image feature value, the type determination result, and the like, and generates a display image. After the generation, the display image generation unit 108 displays the display image on the display device 111.

The input device 110 receives input from the operator. The input device 110 is implemented by a trackball, a button, a touch panel, or the like.

The display device 111 displays the display image generated by the display image generation unit. The display device 111 is implemented by a display, or the like.

The apparatus configuration according to this embodiment is as described above.

(Operation)

Figure 2A:
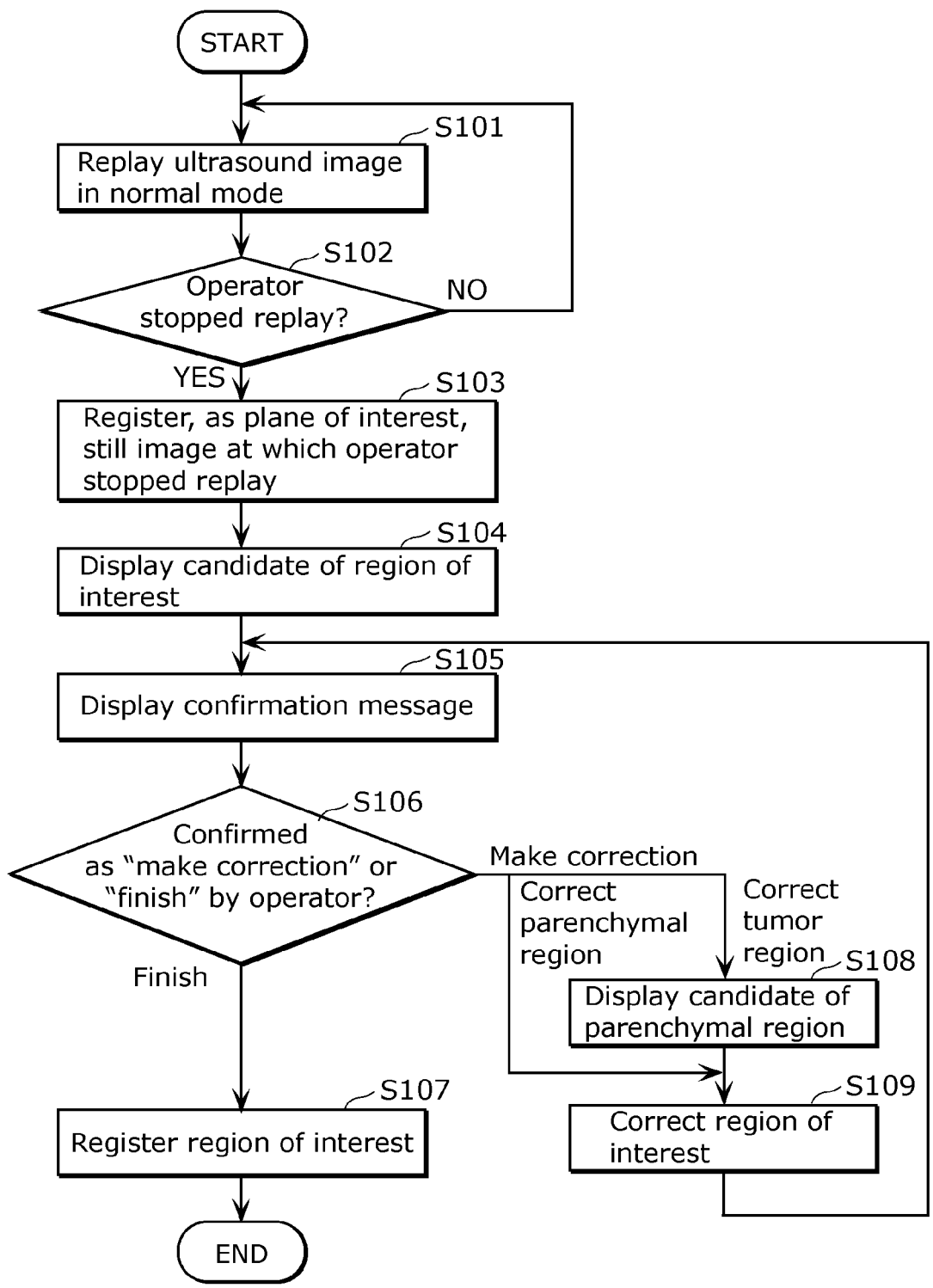
FIG. 2A is a flowchart of operations before administration of a contrast medium according to Embodiment 1.
Figure 2B:
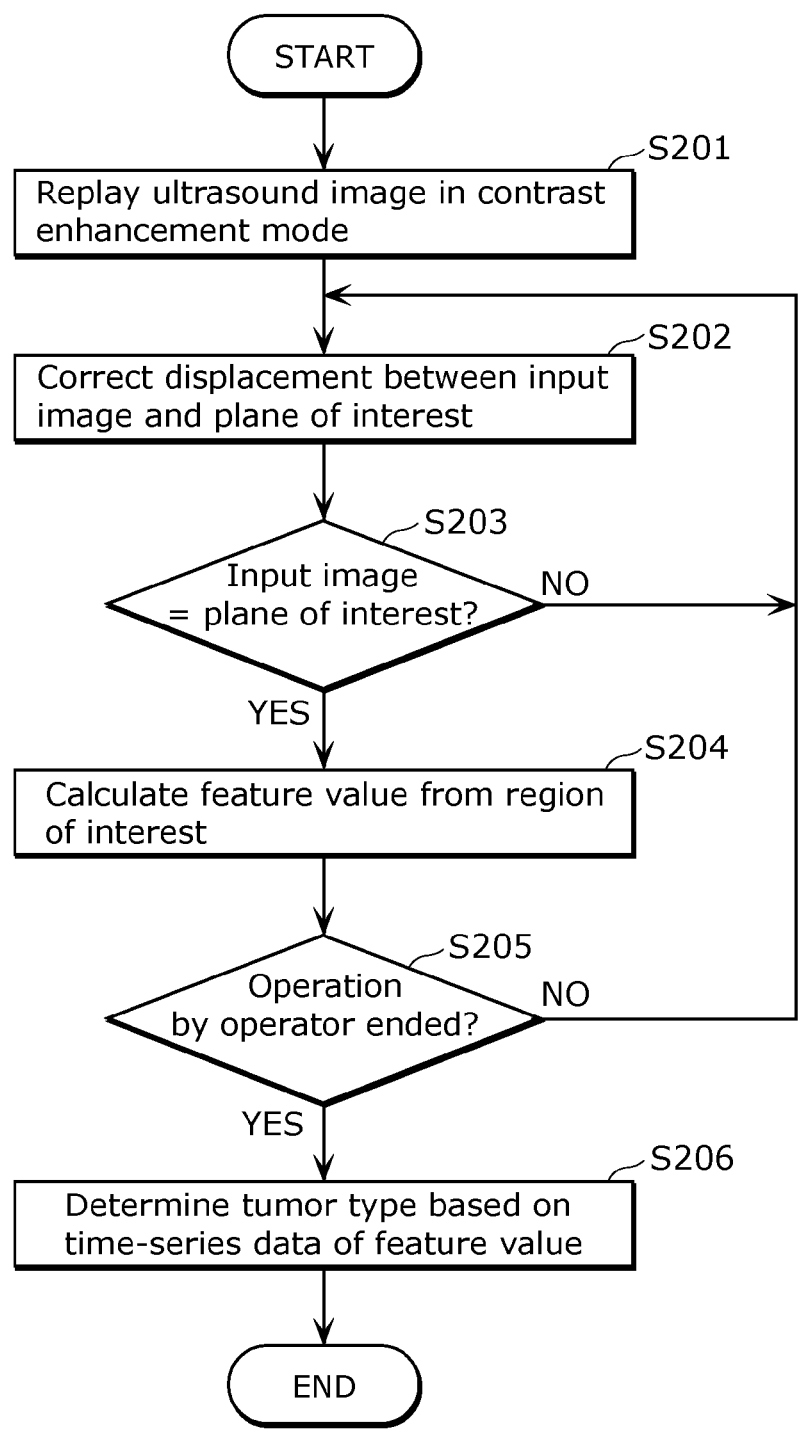
FIG. 2B is a flowchart of operations after administration of the contrast medium according to Embodiment 1.

The following describes the flow of operations according to this embodiment with reference to FIG. 2A and FIG. 2B.

FIG. 2A is a flowchart of operations before the administration of the contrast medium according to this embodiment.

[Step S101]

First, the image forming unit 103 transforms the echo signal output from the ultrasound transmitting and receiving unit 102 into brightness value, and forms an ultrasound image. Then, the image forming unit 103 stores, as the input image, the formed ultrasound image in the data storage unit 104. The display image generation unit 108 reads out, from the data storage unit 104, the input image stored by the image forming unit 103, generates the display image in which patient information, setting information, and the input image are integrated, and then displays the display image on the display device 111. The display mode at this time is referred to as a normal mode. The normal mode indicates the display mode before the administration of the contrast medium.

[Step S102]

In Step S101, the ultrasound diagnostic apparatus receives a command for stopping replay from the operator. When the operator performs, via the input device 110, the operation for stopping the replay, the ultrasound diagnostic apparatus executes Step S103. When the operator does not perform the operation for stopping the replay, the ultrasound diagnostic apparatus returns to Step S101.

[Step S103]

When it is detected that the operator has performed, via the input device 110, the operation for stopping the replay, the ultrasound transmitting and receiving unit 102 stops the operation of ultrasound transmitting and receiving, and the image forming unit 103 stops the operation of image formation. The display image generation unit 108 displays a still image on the display device 111. The region of interest setting unit 105 registers, as the plane of interest, the ultrasound image which is at the time when the replay is stopped and stored in the data storage unit 104.

[Step S104]

Next, when the operator performs the type determination operation via the input device 110, the region of interest setting unit 105 detects, from the plane of interest, candidates of a tumor region and a parenchymal region which are the regions of interest, and stores, in the data storage unit 104, the candidates as the regions of interest. Subsequently, the display image generation unit 108 reads out, from the data storage unit 104, the plane of interest and the region of interest which are stored by the region of interest setting unit 105, generates the display image in which the region of interest is superimposed on the plane of interest, and displays the generated display image on the display device 111. The display image is generated, for example, so that (i) the periphery of the region of interest is indicated by a broken line or (ii) the plane of interest is still visible even if the whole region of interest is colored translucently.

FIG. 3A is an example of the display image in the normal mode. In FIG. 3A, an ultrasound image G11 is displayed on a display image G10. The ultrasound image G11 includes a tumor region G12 and a parenchymal region G13. The ultrasound image G11 is the input image read out from the data storage unit 104. Each of the tumor region G12 and the parenchymal region G13 is the region of interest.

A two-dimensional differential filter is used to detect the candidate of the tumor region. The coefficient of a two-dimensional differential filter is large in a region in which, in the brightness distribution, (i) brightness is low in the center and brightness is high in the surrounding or (ii) brightness is high in the center and brightness distribution is low in the surrounding. The two-dimensional differential filter is moved over the entire screen, and a filter value is calculated at each of the positions. When the tumor region including tumors having different sizes is intended to be detected, resolution of the entire target image is changed to perform detection. For example, when the resolution of the target image is reduced to one-half, twice the size of a tumor is detected. The filter value is calculated at each position, and then the region having the largest filter value is set as the candidate.

The candidate of the parenchymal region shall be in the same depth as the depth of the detected tumor.

Note that the above described the method in which the candidate of the tumor region is detected using the two-dimensional differential filter. Alternatively, the operator may examine the ultrasound image, and set the tumor region.

It should be noted that the examples of the shape of the region of interest are a circular shape and an elliptical shape. However, the shape is not limited to such examples, and the region of interest may be in any shape, such as a polygonal shape including the candidates of the tumor region and the parenchymal region.

Note that the above-described region of interest corresponds to a first region of interest. Furthermore, the above-described parenchymal region corresponds to a third region of interest.

[Step S105]

Next, the display image generation unit 108 displays, on the display device 111, a confirmation message for confirming whether or not the candidate of the region of interest is appropriate.

[Step S106]

Next, the ultrasound diagnostic apparatus receives, via the input device 110, the input which is entered by the operator in response to the confirmation message in Step S13. The operator inputs, in response to the confirmation message, (i) the finish of the setting of the region of interest or (ii) the correction of the parenchymal region or the tumor region.

[Step S107]

When the finish of the setting of the region of interest is entered by the operator, the input value obtainment unit 109 establishes the region of interest stored in the data storage unit 104.

[Step S108]

When the tumor region is corrected via the input device 110 by the operator in response to the confirmation message of Step S105, the region of interest setting unit 105 changes the parenchymal region. Subsequently, the ultrasound diagnostic apparatus executes Step S109.

[Step S109]

When the parenchymal region is corrected via the input device 110 by the operator in response to the confirmation message of Step S105 or when the parenchymal region is corrected in Step S108, the region of interest setting unit 105 corrects the region of interest stored in the data storage unit 104. Subsequently, the ultrasound diagnostic apparatus returns to Step S105, and the display image generation unit 108 displays the confirmation message.

The flowchart regarding the setting of the plane of interest, and the region of interest according to this embodiment is as described above.

FIG. 2B is a flowchart of operations after the administration of the contrast medium according to this embodiment.

[Step S201]

First, after the region of interest of the plane of interest is established in Step S107, the ultrasound transmitting and receiving unit 102 performs transmitting and receiving of the ultrasound which corresponds to the contrast enhancement ultrasound, and the image forming unit 103 forms the image. Specifically, using a conventional pulse inversion imaging, an amplitude modulation imaging (PTLs 2, 3, and 4), or the like, the ultrasound diagnostic apparatus forms a contrast enhanced image in which the reflection echo from the contrast medium is dominant, and a tissue image (an image corresponding to a fundamental component of the received ultrasound) in which a reflection echo from the tissue is dominant. Subsequently, the image forming unit 103 stores the contrast enhanced image and the tissue image in the data storage unit 104. The display image generation unit 108 reads out, from the data storage unit 104, the contrast enhanced image and the tissue image which are stored by the image forming unit 103, and generates the display image in which the contrast enhanced image and the tissue image are arranged side-by-side.

Figures 3B, 3C:
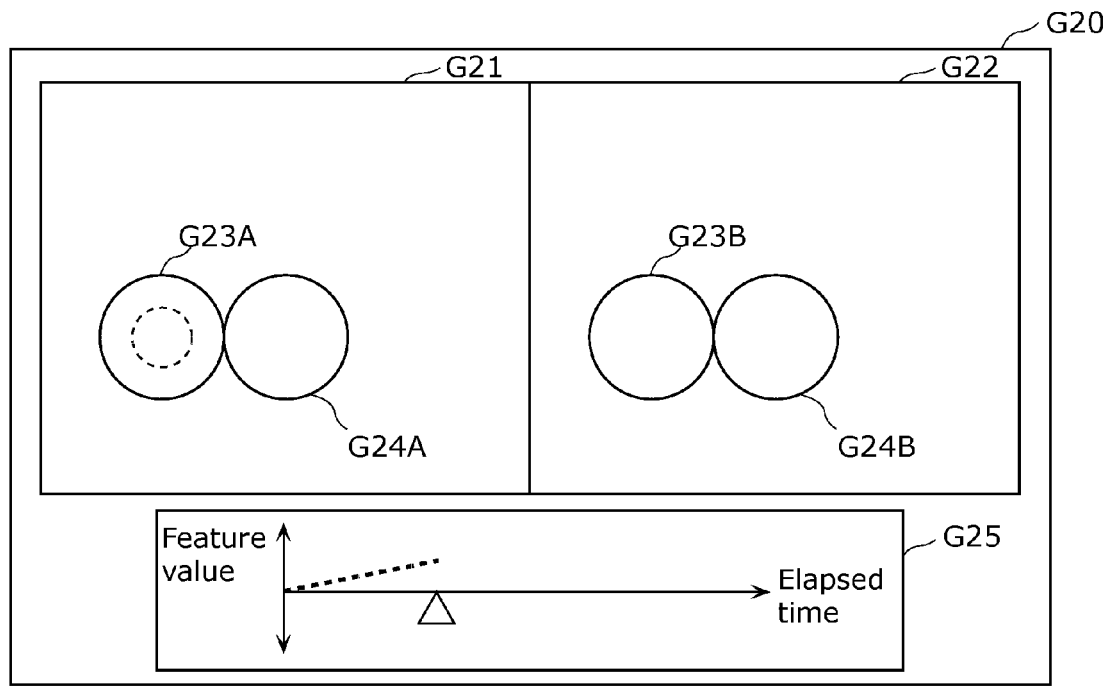
FIG. 3B is another example of the display image according to Embodiment 1.
FIG. 3C is yet another example of the display image according to Embodiment 1.

FIG. 3B is an example of the display image in a contrast enhancement mode. In FIG. 3B, a display image G20 shows a contrast enhanced image G21 and a tissue image G22, which are ultrasound images, and a feature value transition G25. The contrast enhanced image G21 includes a tumor region G23A and a parenchymal region G24A. Furthermore, the tissue image G22 includes a tumor region G23B and a parenchymal region G24B.

The contrast enhanced image G21 and the tissue image G22 are the contrast enhanced image and the tissue image which are read out from the data storage unit 104 and arranged side-by-side. The tumor regions G23A and G23B, and the parenchymal regions G24A and G24B are designated by a system or the operator. The feature value transition G25 displays, in time series, the feature values which are used to determine the type.

The display image generation unit 108 displays, on the display device 111, the generated output image.

[Step S202]

Next, the region of interest setting unit 105 calculates the displacement between the plane of interest and the input image which are stored in the data storage unit 104. The displacement originates from an unsteady movement of a hand of the operator, the heart in a living body, or the breathing. The amount of displacement is calculated using a conventional pattern matching technique. The pattern matching is performed using the tissue image which is formed by the image forming unit 103 in Step S201 and has small reflection echo from the contrast medium.

[Step S203]

Next, the region of interest setting unit 105 determines whether the plane of interest and the input image after the correction of the position which are stored in the data storage unit 104 are the same plane. Here, the region of interest setting unit 105 calculates an error between the images, and determines that the planes are the same, when the error is equal to or less than a threshold value. When it is determined that the planes are the same, the region of interest setting unit 105 corrects, using the amount of displacement calculated in Step S202, the position of the region of interest stored in the data storage unit 104. When the planes are determined to be different, the ultrasound diagnostic apparatus does not calculate the feature value.

[Step S204]

Next, using the input image and the region of interest which are stored in the data storage unit 104, the ultrasound diagnostic apparatus extracts feature values e and r by calculating the feature values e and r which are used to determine the type.

The region of interest includes two regions, namely, a tumor and parenchyma. When the feature value is calculated, a new region of interest is set in the tumor. Note that the new region of interest corresponds to a second region of interest.

The new region of interest may also be determined to correspond to the tumor region. In other words, the new region of interest may be set in the center of the tumor to have one-half of a size of the tumor region. Furthermore, it may be set so that the region of interest and the new region of interest are arranged side-by-side or may be set so that the region of interest is set to surround the new region of interest. Furthermore, the operator may set an arbitrary region.

The following describes the case of setting, as the new region of interest, a region having a size one-half of the size of the tumor region in the center of the tumor region (tumor center region). The difference r between x and y is shown by Expression (1), where x represents average brightness of the tumor region, and y represents average brightness of the new tumor region.

[Math. 1]

$$r = x - y \quad \text{(Expression 1)}$$

Furthermore, the difference e in the average brightness between the tumor region and the parenchymal region is shown by Expression (2), where z represents the average brightness of the parenchymal region.

[Math. 2]

$$e = x - z \quad \text{(Expression 2)}$$

Figure 5:
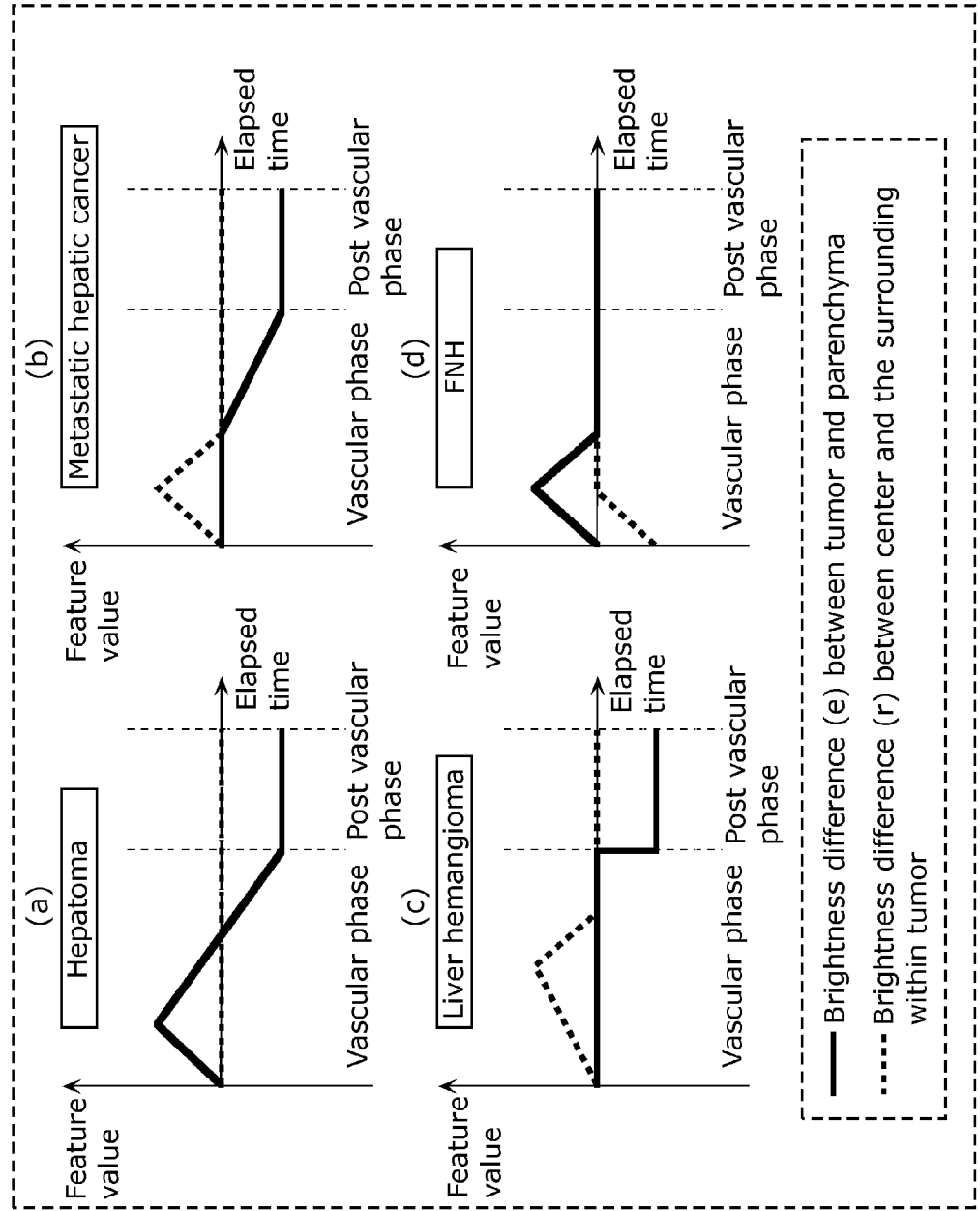
FIG. 5 shows diagrams illustrating examples of feature values of typical examples of the hepatic tumor according to Embodiment 1.

FIG. 5 shows diagrams illustrating examples of feature values e and r on typical examples of the hepatic tumor. In FIG. 5, a positive e indicates that the tumor is hyperechoic compared to the surrounding, whereas a negative e indicates that the tumor is hypoechoic compared to the surrounding. A positive r represents a ring pattern, whereas a negative r represents a center pattern.

Shown in (a) in FIG. 5 are distinctive observations of a hepatoma. The hepatoma shows a homogeneous pattern (more precisely, a basket pattern) in the vascular phase, and is hypoechoic in the post vascular phase. Thus, the value of r is close to zero in the vascular phase, and the value of e is negative in the post vascular phase.

Shown in (b) in FIG. 5 are distinctive observations of a metastatic hepatic cancer. The metastatic hepatic cancer shows a ring pattern in the vascular phase, and is hypoechoic in the post vascular phase. Thus, the value of r is positive in the vascular phase, and the value of e is negative in the post vascular phase.

Shown in (c) in FIG. 5 are distinctive observations of a liver hemangioma. The liver hemangioma changes from the ring pattern to the homogeneous pattern in the vascular phase, and is hypoechoic in the post vascular phase. Thus, the value of r changes from positive to zero in the vascular phase, and the value of e is negative in the post vascular phase.

Shown in (d) in FIG. 5 are distinctive observations of a focal nodular hyperplasia (FNH). The FNH has a spoke-wheel pattern that spreads from the center toward the outside in the vascular phase, and is isoechoic in the post vascular phase. Thus, the value of r changes from negative to zero in the vascular phase, and the value of e is close to zero in the post vascular phase.

As described, it is possible to follow the distinctive observations of the hepatic tumor by using the value of e and the value of r.

[Step S205]

Next, the ultrasound diagnostic apparatus receives an operation from the operator. When the operator inputs an end of the operation, the ultrasound diagnostic apparatus executes Step S206.

[Step S206]

Next, the type determination unit 107 determines the tumor type based on the learning data and the feature value of the period from the vascular phase to the post vascular phase which are stored in the data storage unit 104.

The type determination is performed using a feature value, which is identified beforehand, of a predetermined section of interest.

Figure 6:
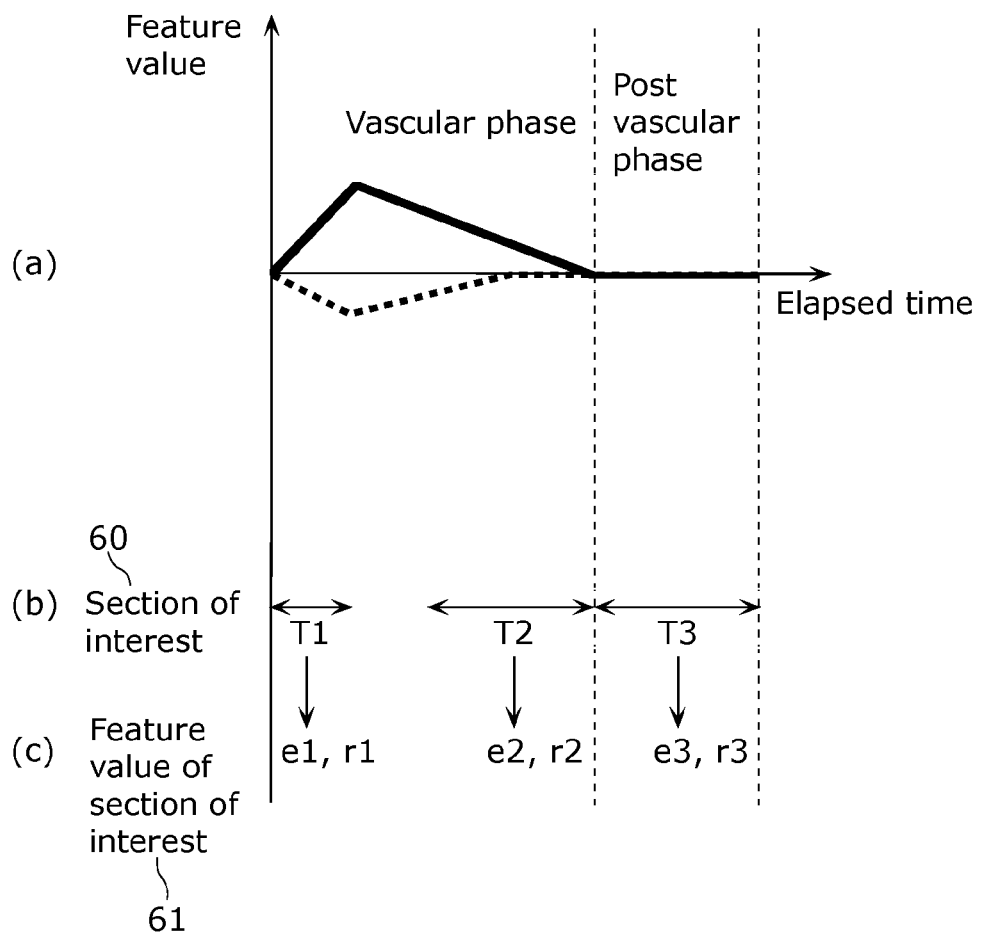
FIG. 6 is a diagram for describing a tumor type determination based on the feature value according to Embodiment 1.
Figure 7A:
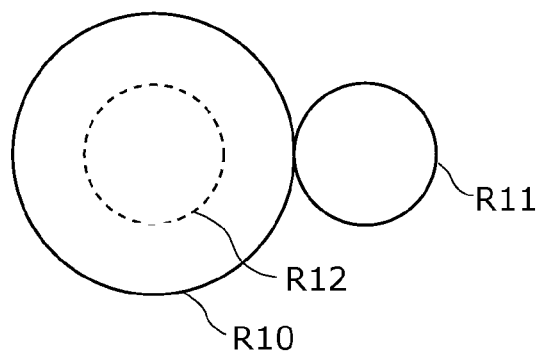
FIG. 7A is a diagram for describing the feature value according to Embodiment 1.
Figure 7B:
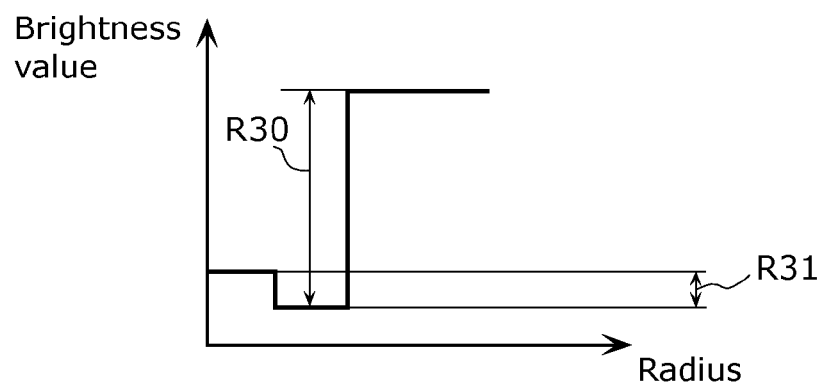
FIG. 7B is a diagram for describing the feature value according to Variation 1 of Embodiment 1.

FIG. 6 is a diagram for describing a tumor type determination based on the feature value according to Embodiment 1. T1 to T3 are sections of interest used for determining the type. The values e1 to e3, and the values r1 to r3 are respectively average values of the values of e and the values of r in each of the sections of interest. In an example shown in FIG. 6, the tumor type is determined based on six input parameters. Here, description is given of the case in which the determination is made using a conventional support vector machine (linear). Expression (3) is satisfied, where w(i) and b(i) represent learning data of type i, m(i) represents an evaluation value, and x represents an input parameter.

[Math. 3]

$$m(i) = \vec{w}(i) \cdot \vec{x} - \vec{b}(i) \quad \text{(Expression 3)}$$

Here, each of w(i) and b(i) is learning data calculated using the support vector machine and is prepared for each of types i. Details of the learning method are omitted. When determining the tumor type from input data, the evaluation value m(i) is calculated for each of the types. Then, the tumor type of the input data is determined to be the type on which the evaluation value m(i) is the greatest.

The flowchart after the administration of the contrast medium according to this embodiment is as described above.

It should be noted that the candidate of the parenchymal region is the region close to the tumor region in the same depth in the above description. However, the candidate is not limited to such a region. For example, when hyperechoic region, such as the region including the diaphragm, exists in a region close to the tumor region in the same depth, a region in a different depth may be selected as the parenchymal region.

Furthermore, in the calculation of the difference in brightness between the tumor region and the parenchymal region, the brightness value of the tumor region may be calculated, for example, from the tumor center region used in the feature value extraction of the ring pattern, instead of from the entire tumor.

It should be noted that the average brightness of each region is used in extraction of the feature value. However, information on other brightness may be used. The information on other brightness may be, for example, brightness of a dot at a predetermined position in the region, the median value of brightness of the region, or a mode of brightness of the region.

Furthermore, in associating the feature value and the tumor type, the section of interest may be changed according to the type of the tumor.

Furthermore, although the support vector machine is used to associate the feature value and the tumor type, the means for association is not limited to the use of the support vector machine, but other machine learning may be used.

(Advantageous Effects)

As described above, the ultrasound diagnostic apparatus according to an aspect of the present invention can determine the type of the tumor based on the difference in brightness between the two regions of interest which are set in a target region (tumor region) in the ultrasound image and which show significant feature according to the type of the tumor. At this time, determination is made based on the difference in brightness between the two regions of interest. In this way, the determination result is less likely to be affected by gain or the like of the ultrasound probe, and the strength of the pattern can be accurately evaluated. Thus, it is possible to calculate the difference in brightness between the two regions of interest in the ultrasound image obtained from the subject, and determine the type of the tumor which matches the calculated difference in brightness. Thus, it is possible to determine the type of a hepatic tumor with high accuracy without depending on the reader of the ultrasound image.

Furthermore, it is possible to determine the type of the tumor based on the difference in brightness between the tumor region and the parenchymal region in the ultrasound image. Here, since the tumor region and the parenchymal region are set, the type of the tumor can be determined based on not only the brightness of the tumor region, but also based on the difference in brightness between the tumor region and the parenchymal region. Thus, it is possible to determine the type of the hepatic tumor with high accuracy.

Furthermore, it is possible to regard the tumor region in the ultrasound image as being approximately elliptical in shape, set the region of interest in each of the center area and the surrounding area of the elliptical shape, calculate the difference in brightness between the regions of interest, and determine the type of the tumor which matches the calculated difference in brightness. Thus, it is possible to determine the type of the hepatic tumor more accurately.

Furthermore, it is possible to regard the tumor region in the ultrasound image as being approximately circular in shape, set the region of interest in each of the center area and the surrounding area of the circular shape, calculate the difference in brightness between the regions of interest, and determine the type of the tumor which matches the calculated difference in brightness. Thus, it is possible to determine the type of the hepatic tumor more accurately.

Furthermore, the difference in brightness between the regions of interest in a predetermined period (e.g. an arterial phase and the portal phase in the vascular phase; and the post vascular phase) during which the contrast enhancement pattern by the contrast medium is distinctive is used. This increases the accuracy in determining the type of the tumor. Thus, it is possible to determine the type of the hepatic tumor with high accuracy.

Furthermore, it is possible to determine the type of the tumor based on the feature value. A specific example of the association between the predetermined feature value and the type of the target tissue is learning data which is based on the past cases.

Furthermore, the feature value appropriate for the type determination of the hepatic tumor is used. Thus, it is possible to determine the representative case of the hepatic tumor, such as the hepatoma, the metastatic hepatic cancer, the liver hemangioma, or the focal nodular hyperplasia (FNH).

Variation 1 of this Embodiment

Embodiment 1 described an example in which the region of interest is set for each of the tumor region and a tumor center region, and then the average brightness is calculated for each of the regions of interest. The difference in the average brightness between the regions of interest is set as the feature value r of the ring pattern. However, since the tumor center region is set corresponding to the tumor region, the effects of the setting position or the shape of the tumor region on the feature value is not small. In view of this, the following describes a method for reducing the effects in the extraction of the feature value. It should be noted that the tumor region and the tumor center region may be in any shape. The tumor region and the tumor center region may be, for example, circular in shape or elliptical in shape. The following describes the case of the circular shape.

(Configuration)

A system configuration is the same as the system configuration of Embodiment 1. Thus, the descriptions thereof are omitted.

(Operation)

Figure 2C:
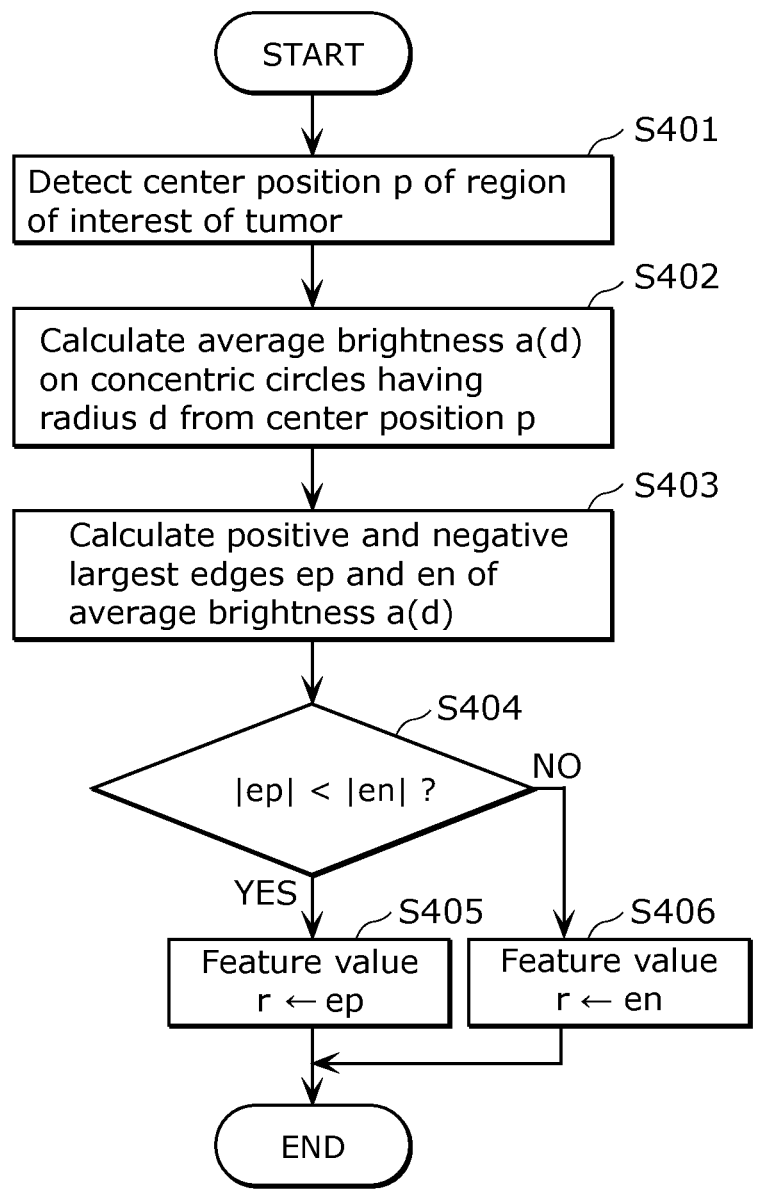
FIG. 2C is a flowchart of operations regarding feature value extraction according to Variation 1 of Embodiment 1.

FIG. 2C is a flowchart of operations regarding a feature value extraction according to this variation.

The following describes process performed by the feature value extraction unit 106.

[Step S401]

First, the feature value extraction unit 106 identifies a center position p of the tumor which has been set as the region of interest.

[Step S402]

Next, the feature value extraction unit 106 calculates an average brightness a(d) on concentric circles having radius d from the center position p. This is referred to as a radius brightness distribution a(d). Here, the calculation range includes up to the contour of the tumor that is set as the region of interest.

[Step S403]

Next, in the radius brightness distribution a(d), a positive largest edge ep and a negative largest edge en in a radial direction are calculated. An edge e(d) at a position d is shown by Expression (4).

[Math. 4]

$$e(r) = \sum_{i}^{n} a(d+1+i) - \sum_{i}^{n} a(d-i) \qquad \text{(Expression 4)}$$

Here, after summing n samples, subtraction is performed to increase the resistance to noise, where i represents the number of the samples. For example, n is set to several percent of the size of the region of interest. The largest value among positive values of e(d) is ep, and the smallest value among negative values of e(d) is en.

[Steps S404, S405 and S406]

Next, the absolute values of the positive edge ep and the negative edge en are compared to each other, and the larger one of the edges is set to the feature value r.

The operations regarding the feature value extraction according to Variation 1 of this embodiment is as described above.

It should be noted that, out of the positive edge ep and the negative edge en, the position (radius) d of the edge having a larger absolute value may be set to a new feature value to be used together with the feature value r and the like, for the determination of the tumor.

It should be noted that assuming that, out of the positive edge ep and the negative edge en, the position (radius) d of the edge having a larger absolute value is a boundary, the tumor center region may be set on the side closer to the center part of the tumor relative to the boundary.

(Advantageous Effects)

As described above, the ultrasound diagnostic apparatus according to an aspect of the present invention can determine the type of the tumor based on the brightness gradient in a direction toward the surrounding area from the center area of the tumor region (or a direction toward the center area from the surrounding area), without depending on the position or the shape of the center area of the tumor region. Thus, it is possible to determine the type of the hepatic tumor with high accuracy.

Furthermore, it is possible to determine the type of the tumor based on the size of the radius at which the brightness gradient is greatest in a direction toward the surrounding area from the center area of the tumor (or a direction toward the center area from the surrounding area). Thus, it is possible to determine the type of the hepatic tumor with high accuracy.

Furthermore, it is possible to set, as the regions of interest, two regions having large difference between each other in the average brightness. Use of these two regions of interest makes it possible to increase the accuracy in determining the type of the tumor. Thus, it is possible to determine the type of the hepatic tumor with high accuracy.

(Other Variations)

Note that the present invention has thus far been described based on the embodiment above. However, naturally, the present invention is not limited to the above embodiment. The following case is also included in the present invention.

(1) Each of the above apparatuses is, specifically, a computer system that includes a microprocessor, a ROM, a RAM, a hard disk unit, a display unit, a keyboard, a mouse, and the like. A computer program is stored in the ROM or the hard disk unit. Functions of each of the apparatuses can be achieved by the microprocessor operating in accordance with the computer program. The computer program mentioned here is a combination of a plurality of instruction codes that represent instructions to a computer for achieving predetermined functions.

(2) Part or all of the structural elements included in each of the above apparatuses may be provided in one system LSI (Large Scale Integration). The system LSI is an ultra-multi-functional LSI produced by integrating a plurality of components on one chip, and is, specifically, a computer system that includes a microprocessor, a ROM, a RAM, and the like. A computer program is stored in the ROM. Functions of the system LSI can be achieved by the microprocessor operating in accordance with the computer program.

(3) Part or all of the structural elements included in each of the above apparatuses may be provided in an IC card or a single module that is removably connectable to the apparatus. The IC card or the module is a computer system that includes a microprocessor, a ROM, a RAM, and the like. The IC card or the module may include the above-mentioned ultra-multi-functional LSI. Functions of the IC card or the module can be achieved by the microprocessor operating in accordance with the computer program. The IC card or the module may be tamper resistant.

(4) The present invention may also be the method described above. The present invention may also be a computer program that realizes the method by a computer. The present invention may also be a digital signal including the computer program.

The present invention may also be a computer-readable recording medium, such as a flexible disk, a hard disk, a CD-ROM, an MO, a DVD, a DVD-ROM, a DVD-RAM, a BD (Blu-ray Disc), or a semiconductor memory, on which the computer program or the digital signal is recorded. In addition, the present invention may be the digital signal recorded on such a recording medium.

The present invention may also be the computer program or the digital signal transmitted via an electric communication line, a wired or wireless communication line, a network, such as the Internet, data broadcasting, and the like.

The present invention may also be a computer system that includes a microprocessor and a memory. In this case, the computer program may be stored in the memory, and the microprocessor may operate in accordance with the computer program.

The computer program or the digital signal may be provided to another independent computer system by distributing the recording medium on which the computer program or the digital signal is recorded, or by transmitting the computer program or the digital signal via the network and the like. The independent computer system may then execute the computer program or the digital signal to function as the present invention.

(5) The above embodiment and variations may be combined with each other.

In the exemplary embodiment, each of the structural elements may be implemented as a piece of dedicated hardware or implemented by executing a software program appropriate for the structural element. The structural elements may also be implemented by a program execution unit, such as a CPU or a processor, which reads and executes a software program recorded on a recording medium, such as a hard disk or a semiconductor memory. Here, the ultrasound diagnostic apparatus and the like in the above-described embodiment are implemented by executing a software program below.

Specifically, the program causes a computer to execute an ultrasound diagnostic method which determines a type of target tissue inside a body of a subject, the ultrasound diagnostic method includes: forming an ultrasound image which corresponds to an echo signal received from the subject to which a contrast medium has been administered; setting, in a target region corresponding to the target tissue on the ultrasound image formed in the forming, a first region of interest and a second region of interest which are two regions different from each other; extracting, as a feature value, a difference in brightness between the first region of interest and the second region of interest set in the setting; and determining, based on the feature value extracted in the extracting, the type of the target tissue.

The ultrasound diagnostic apparatus according to one of or more of the aspects of the present invention have been described based on the embodiment. However, the present invention is not limited to such an embodiment. Various modifications of the exemplary embodiment as well as embodiments resulting from arbitrary combinations of structural elements of different exemplary embodiments that may be conceived by those skilled in the art may also be included within the scope according to one of or more of the aspects of the present invention as long as these do not depart from the essence of the present invention.

INDUSTRIAL APPLICABILITY

A tumor type determination method and a tumor type determination method according to the present invention are applicable to a qualitative diagnosis using contrast enhanced ultrasound.

REFERENCE SIGNS LIST

1 Ultrasound diagnostic apparatus
60 Section of interest
61 Feature value of section of interest
80 Predetermined pattern
81 Input pattern
101 Ultrasound probe
102 Ultrasound transmitting and receiving unit
103 Image forming unit
104 Data storage unit
105 Region of interest setting unit
106 Feature value extraction unit
107 Type determination unit
108 Display image generation unit
109 Input value obtainment unit
110 Input device
111 Display device
G10 Display image (normal mode)
G11 Ultrasound image
G12, G23A, G23B, R10 Region of interest of tumor
G13, G24A, G24B, R11 Region of interest of parenchyma
G20 Display image (contrast enhancement mode)
G21 Contrast enhanced image
G22 Tissue image
G25 Feature value transition
R12 Region of interest of tumor center
R30 Positive largest edge
R31 Negative largest edge

The invention claimed is:

1. An ultrasound diagnostic apparatus which determines a type of target tissue inside a body of a subject, the ultrasound diagnostic apparatus comprising:
an ultrasound probe which transmits ultrasound to the subject; and
a processor or integrated circuit which is configured to:
form an ultrasound image which corresponds to an echo signal received by the ultrasound probe from the subject to which a contrast medium has been administered;
set, in a target region corresponding to the target tissue on the ultrasound image, a first region of interest and a second region of interest which are two regions different from each other, wherein the first region of interest and the second region of interest are set such that the first region of interest surrounds an outer periphery of the second region of interest;
extract feature values including a first feature value and a second feature value, the first feature value being a difference in brightness between the first region of interest and the second region of interest within a predetermined first time period, and the second feature value being a difference in brightness between the first region of interest and the second region of interest within a predetermined second time period; and
determine, based on at least each of the first feature value and the second feature value, the type of the target tissue.

2. The ultrasound diagnostic apparatus according to claim 1, wherein:
the processor or integrated circuit is further configured to set a third region of interest outside the target region on the ultrasound image,
the feature values extracted by the processor or integrated circuit further include, in addition to the first feature value and the second feature value, a third feature value and a fourth feature value, the third feature value being a difference in brightness between the first region of interest and the third region of interest within the first time period, and the fourth feature value being a difference in brightness between the first region of interest and the third region of interest within the second time period, and
the processor or integrated circuit determines the type of the target tissue based on at least each of the first feature value, the second feature value, the third feature value, and the fourth feature value.

3. The ultrasound diagnostic apparatus according to claim 1, wherein the processor or integrated circuit is further configured to extract, as the difference in brightness, a brightness gradient having a largest absolute value in a direction (i) toward a surrounding area from a center area in the target region or (ii) toward the center area from the surrounding area in the target region.

4. The ultrasound diagnostic apparatus according to claim 1, wherein the processor or integrated circuit is configured to set (i) the second region of interest to be centered on a center area of the target region and to be approximately elliptical in shape, and (ii) the first region of interest to be centered on the center area of the target region, to be approximately elliptical in shape, to include a region larger than the second region, and to exclude the second region of interest.

5. The ultrasound diagnostic apparatus according to claim 1, wherein the processor or integrated circuit is configured to set (i) the second region of interest to be centered on a center area of the target region and to be approximately circular in shape, and (ii) the first region of interest to be centered on the center area of the target region, to be approximately circular in shape, to include a region larger than the second region, and to exclude the second region of interest.

6. The ultrasound diagnostic apparatus according to claim 1, wherein the feature values extracted by the processor or integrated circuit further include, in addition to the first feature value and the second feature value, a distance between a center area of the target region and a position at which an absolute value of brightness gradient is largest in a direction toward a surrounding area from the center area in the target region or in a direction toward the center area from the surrounding area in the target region.

7. The ultrasound diagnostic apparatus according to claim 1, wherein the processor or integrated circuit is configured to (i) set the second region of interest on a side closer to a center area relative to a position at which an absolute value of a brightness gradient is largest in a direction toward a surrounding area from the center area in the target region, and (ii) set the first region of interest on a side further from the center area relative to the position.

8. The ultrasound diagnostic apparatus according to claim 1, wherein the processor or integrated circuit is configured to determine, by referring to an association between a plurality of patterns of a feature value and a plurality of types of the target tissue, the type of the target tissue to be a type which corresponds to one of the patterns that matches the extracted feature values.

9. The ultrasound diagnostic apparatus according to claim 1, wherein the processor or integrated circuit is configured to determine, based on the feature values, the type of the target tissue to be one of a hepatoma, a metastatic hepatic cancer, a liver hemangioma, and a focal nodular hyperplasia (FNH).

10. The ultrasound diagnostic apparatus according to claim 1, wherein:
the feature values extracted by the processor or integrated circuit include, in addition to the first feature value and the second feature value, a third feature value, the third feature value being a difference in brightness between the first region of interest and the second region of interest within a predetermined third time period, and
the processor or integrated circuit determines the type of the target tissue based on only the first feature value, the second feature value, and the third feature value.

11. The ultrasound diagnostic apparatus according to claim 1, further comprising:
a data storage storing data usable for determining the type of the target tissue,
wherein the processor or integrated circuit determines the type of the target tissue by substituting the data in the data storage, the first feature value, and the second feature value into a mathematical expression usable for determining the type of the target tissue.

12. An ultrasound diagnostic method for an ultrasound diagnostic apparatus comprising an ultrasound probe which transmits ultrasound to a subject, wherein the ultrasound diagnostic method determines a type of target tissue inside a body of the subject, the ultrasound diagnostic method comprising:
forming an ultrasound image which corresponds to an echo signal received by the ultrasound probe from the subject to which a contrast medium has been administered;
setting, in a target region corresponding to the target tissue on the ultrasound image formed in the forming, a first region of interest and a second region of interest which are two regions different from each other, wherein the first region of interest and the second region of interest are set such that the first region of interest surrounds an outer periphery of the second region of interest;
extracting feature values including a first feature value and a second feature value, the first feature value being a difference in brightness between the first region of interest and the second region of interest within a predetermined first time period, and the second feature value being a difference in brightness between the first region of interest and the second region of interest within a predetermined second time period; and
determining, based on at least each of the first feature value and the second feature value, the type of the target tissue.

13. A non-transitory computer-readable recording medium having a computer program recorded thereon for causing a computer of an ultrasound diagnostic apparatus to execute an ultrasound diagnostic method which determines a type of target tissue inside a body of a subject, the ultrasound diagnostic apparatus comprising an ultrasound probe which transmits ultrasound to the subject, the program causing the computer to execute the ultrasound diagnostic method comprising:
forming an ultrasound image which corresponds to an echo signal received by the ultrasound probe from the subject to which a contrast medium has been administered;
setting, in a target region corresponding to the target tissue on the ultrasound image formed in the forming, a first region of interest and a second region of interest which are two regions different from each other, wherein the first region of interest and the second region of interest are set such that the first region of interest surrounds an outer periphery of the second region of interest;
extracting feature values including a first feature value and a second feature value, the first feature value being a difference in brightness between the first region of interest and the second region of interest within a predetermined first time period, and the second feature value being a difference in brightness between the first region of interest and the second region of interest within a predetermined second time period; and
determining, based on at least each of the first feature value and the second feature value, the type of the target tissue.

14. An ultrasound diagnostic apparatus which determines a type of target tissue inside a body of a subject, the ultrasound diagnostic apparatus comprising:
an ultrasound probe which transmits ultrasound to the subject; and
a processor or integrated circuit which is configured to:
form an ultrasound image which corresponds to an echo signal received by the ultrasound probe from the subject to which a contrast medium has been administered;
set a first region of interest in a target region which corresponds to the target tissue on the ultrasound image, and a third region of interest outside the target region on the ultrasound image;
extract feature values including a third feature value and a fourth feature value, the third feature value being a difference in brightness between the first region of interest and the third region of interest within a predetermined first time period, and the fourth feature value being a difference in brightness between the first region of interest and the third region of interest within a predetermined second time period; and
determine, based on at least each of the third feature value and the fourth feature value, the type of the target tissue.

15. The ultrasound diagnostic apparatus according to claim 14, wherein the processor or integrated circuit is configured to set the first region of interest and the third region of interest such that a part of the first region of interest and a part of the third region of interest are located at a same depth.

16. The ultrasound diagnostic apparatus according to claim 14, wherein the processor or integrated circuit is configured to set each of the first region of interest and the third region of interest so as to be approximately circular or elliptical in shape.

17. The ultrasound diagnostic apparatus according to claim 14, wherein:
the first time period is earlier in time than the second time period, and
when the third feature value is calculated by subtracting a brightness of the third region of interest within the first time period from a brightness of the first region of interest within the first time period, and the fourth feature value is calculated by subtracting a brightness of the third region of interest within the second time period from a brightness of the first region of interest within the second time period, the processor or integrated circuit determines that the type of the target tissue is a predetermined first type when the third feature value is a positive value and the fourth feature value is a negative value.

18. The ultrasound diagnostic apparatus according to claim 14, wherein:
the first time period is earlier in time than the second time period, when the third feature value is calculated by subtracting a brightness of the third region of interest within the first time period from a brightness of the first region of interest within the first time period, and the fourth feature value is calculated by subtracting a brightness of the third region of interest within the second time period from a brightness of the first region of interest within the second time period, the processor or integrated circuit determines that the type of the target tissue is a predetermined second type when the third feature value is zero and the fourth feature value is a negative value.

19. The ultrasound diagnostic apparatus according to claim 14, wherein
the feature values extracted by the processor or integrated circuit include, in addition to the third feature value and the fourth feature value, a fifth feature value, the fifth feature value being a difference in brightness between the first region of interest and the third region of interest within a predetermined third time period, and
the processor or integrated circuit determines the type of the target tissue based on only the third feature value, the fourth feature value, and the fifth feature value.

20. The ultrasound diagnostic apparatus according to claim 14, further comprising:
a data storage storing data usable for determining the type of the target tissue,
wherein the processor or integrated circuit determines the type of the target tissue by substituting the data in the data storage, the third feature value, and the fourth feature value into a mathematical expression usable for determining the type of the target tissue.

21. An ultrasound diagnostic method for an ultrasound diagnostic apparatus comprising an ultrasound probe which transmits ultrasound to a subject, wherein the ultrasound diagnostic method determines a type of target tissue inside a body of a subject, the ultrasound diagnostic method comprising:
forming an ultrasound image which corresponds to an echo signal received by the ultrasound probe from the subject to which a contrast medium has been administered;
setting a first region of interest in a target region which corresponds to the target tissue on the ultrasound image formed in the forming, and a third region of interest outside the target region on the ultrasound image;
extracting feature values including a third feature value and a fourth feature value, the third feature value being a difference in brightness between the first region of interest and the third region of interest within a predetermined first time period, and the fourth feature value being a difference in brightness between the first region of interest and the third region of interest within a predetermined second time period; and
determining, based on at least each of the third feature value and the fourth feature value, the type of the target tissue.

22. A non-transitory computer-readable recording medium having a computer program recorded thereon for causing a computer to execute the ultrasound diagnostic method according to claim 21.

23. The ultrasound diagnostic method according to claim 21, wherein the first region of interest and the third region of interest are set such that a part of the first region of interest and a part of the third region of interest are located at a same depth.

\* \* \* \* \*